United States Patent
Stauch et al.

(10) Patent No.: US 8,386,018 B2
(45) Date of Patent: *Feb. 26, 2013

(54) MEDICAL DEVICE FOR DETERMINING THE POSITION OF INTRACORPOREAL IMPLANTS

(75) Inventors: Roman Stauch, Assamstadt (DE); Miroslaw Wrobel, Karlstadt (DE)

(73) Assignee: Wittenstein AG, Igersheim (DE)

( * ) Notice: Subject to any disclaimer, the term of this patent is extended or adjusted under 35 U.S.C. 154(b) by 1245 days.

This patent is subject to a terminal disclaimer.

(21) Appl. No.: 11/952,230

(22) Filed: Dec. 7, 2007

(65) Prior Publication Data

US 2008/0146926 A1    Jun. 19, 2008

(30) Foreign Application Priority Data

Dec. 13, 2006 (DE) .......................... 10 2006 059 225

(51) Int. Cl.
*A61B 5/05* (2006.01)

(52) U.S. Cl. ............. 600/424; 606/53; 606/60; 606/246

(58) Field of Classification Search ................... 600/424; 606/53, 60, 246, 250–261
See application file for complete search history.

(56) References Cited

U.S. PATENT DOCUMENTS

| | | | | | |
|---|---|---|---|---|---|
| 5,967,980 | A | * | 10/1999 | Ferre et al. | 600/424 |
| 6,161,032 | A | * | 12/2000 | Acker | 600/424 |
| 7,520,879 | B2 | * | 4/2009 | Justis et al. | 606/86 A |
| 2006/0173251 | A1 | * | 8/2006 | Govari et al. | 600/306 |
| 2007/0016007 | A1 | * | 1/2007 | Govari et al. | 600/424 |

* cited by examiner

*Primary Examiner* — James Kish
(74) *Attorney, Agent, or Firm* — Bachman & LaPointe, P.C.

(57) ABSTRACT

A medical device for determining the position of intracorporeal implants such as fixation systems, plates or the like, comprises at least one impedance-measuring device and an ultrasound device which are both connected to at least one intracorporeal probe, the impedance-measuring device being additionally equipped with at least one connector for connection to the implant. The device is suitable for determining the position of pedicle screws and the like in a spinal column fixation system with metal rods as stabilizers.

5 Claims, 1 Drawing Sheet

MEDICAL DEVICE FOR DETERMINING THE POSITION OF INTRACORPOREAL IMPLANTS

BACKGROUND OF THE INVENTION

The invention relates to a medical device for determining the position of intracorporeal implants such as fixation systems, plates or the like.

In the medical treatment of spinal fractures, for example, which can be caused by falls, osteoporosis, tumors, etc., various kinds of fixation systems are used in which screws with an eyelet, referred to as pedicle screws, are used, the fixation rods being inserted through their respective eyelets.

In the conventional operating procedure, the pedicle screws and fixation rods are introduced by detaching large areas of the muscles from the spinal column, the pedicle screws being screwed into the vertebral body of the spinal column on both sides of the vertebral canal, and the fixation rods being inserted from the top downward through the eyelets of the pedicle screws.

In young patients, the fixation rods are removed after about six months, since otherwise there is a danger of the screws/rods breaking with the increasing mobility of the patient.

In older patients, for example with osteoporotic damage (fractures, sintering) of the spinal column, permanent fusion is often generally carried out by treatment with a rod system (internal fixator, optionally in combination with bone cement) or a plate system according to the fixator principle. However, there is a danger here of the screws breaking through into the intervertebral disc space because of the reduced bone strength in osteoporosis.

By contrast, in the so-called minimally invasive method, the spinal column is not exposed, and instead the treatment is performed from the outside, only through small incisions in the skin. This method includes, for example, vertebroplasty, in which bone cement is injected into the vertebral bodies without these being straightened beforehand, or kyphoplasty, in which collapsed vertebrae are straightened with the aid of an inflatable balloon and then with injected biological cement. By contrast, the introduction of fixation rods in the treatment of fractures of the vertebral bodies has not hitherto been possible by a minimally invasive procedure.

The object of the invention is to make it possible to determine the position of intracorporeal implants in a simple way, without the need for major surgical procedures.

SUMMARY OF THE INVENTION

According to the invention, this object is achieved by using a medical device comprising an impedance-measuring device and an ultrasound device which are both connected to at least one intracorporeal probe, the impedance-measuring device additionally being equipped with at least one connector for electrically conductive connection to the implant.

According to the invention, the measurement parameter used in the impedance measurement for determining the position is the phase displacement between current and voltage that occurs as a function of the distance between the intracorporeal probe and the implant, i.e. if it is small, this means a small distance, and if it is large, this means a large distance. As a result, the size of the impedance is a function of the distance between probe and implant.

The combination of impedance measurement and ultrasound has the advantage that the impedance-measuring device can be used for a rough determination of position and the ultrasound device can be used for a precise determination of position, where a rough determination of position is to be understood as the first approach of the probe to the implant, whereas the remaining path of the probe as far as the implant, or even into the implant, is effected by precise determination of position with the aid of the ultrasound device.

In other words, taking the analogy of the lighting of a vehicle: "full beam" for the rough positioning by approach via the impedance measurement, where the tissue composition can also be measured, i.e. which tissue is passed and what vitality it has. As soon as a relative approach to the implant is achieved, a switch is made to "dimmed beam" or ultrasound for the more precise positioning.

If several implants are present one behind another for example, it is expedient for the impedance-measuring device and the ultrasound device to be switched on alternately, i.e. the rough determination of position and the precise determination of position take place anew for each consecutive implant.

It is also possible for the impedance-measuring device and the ultrasound device to be switched in such a way that they are simultaneously active, which improves the guiding of the probe.

The main advantage of the medical device according to the invention lies in the use in minimally invasive surgery, since extensive areas of tissue and/or muscle no longer have to be detached, thus resulting in reduced blood loss, less damage to the muscle nerves, preservation of the proprioreception, less scar formation on the skin and muscles, and therefore shorter periods of confinement and earlier mobilization of the patients. Finally, the X-ray burden for physician and patient during intraoperative application can also be reduced by the use of ultrasound technology.

The device according to the invention is suitable in particular for determining the position in a spinal column fixation system with rods as stabilizers and with so-called pedicle screws in minimally invasive surgery, the rods serving specifically as intracorporeal probes with which the impedance-measuring device and the ultrasound device are connected, while the additional connector of the impedance-measuring device is electrically conductively connected to the pedicle screws.

It is expedient for the intracorporeal probe to have a rod-shaped design and, at its free hand end, essentially to have an ultrasound head and a measurement transducer, these being secured to the probe by a thread, a bayonet catch or the like, such that they can be removed again at the end of an operation. At the same time, however, it must be ensured that this threaded connection cannot come loose during manipulation in an operation, which in particular must not be allowed to happen upon rotation of the probe to the left and right, for which reason a suitable fine thread is to be preferred here. Moreover, cut grooves in the rod are necessary for focusing the ultrasound, and these can be located also in the handpiece.

The device according to the invention is operated as follows: first, during its intracorporeal introduction, the probe is used for a rough determination of position, specifically with the aid of the impedance-measuring device measuring the phase displacement between current and voltage as a function of the distance between the probe and the implant, whereas, shortly before the implant is reached by the probe, a precise determination of position is carried out with the aid of the ultrasound device.

BRIEF DESCRIPTION OF THE DRAWINGS

Further features and advantages of the present invention will become clear from the following description of an illustrative embodiment in which reference is made to the drawings, which shows a FIG. 1 in which the side view of a portion of a spinal column is indicated schematically, where three vertebral bodies can be connected to one another in accordance with the invention, i.e. can be stabilized.

DETAILED DESCRIPTION

Figure 1:
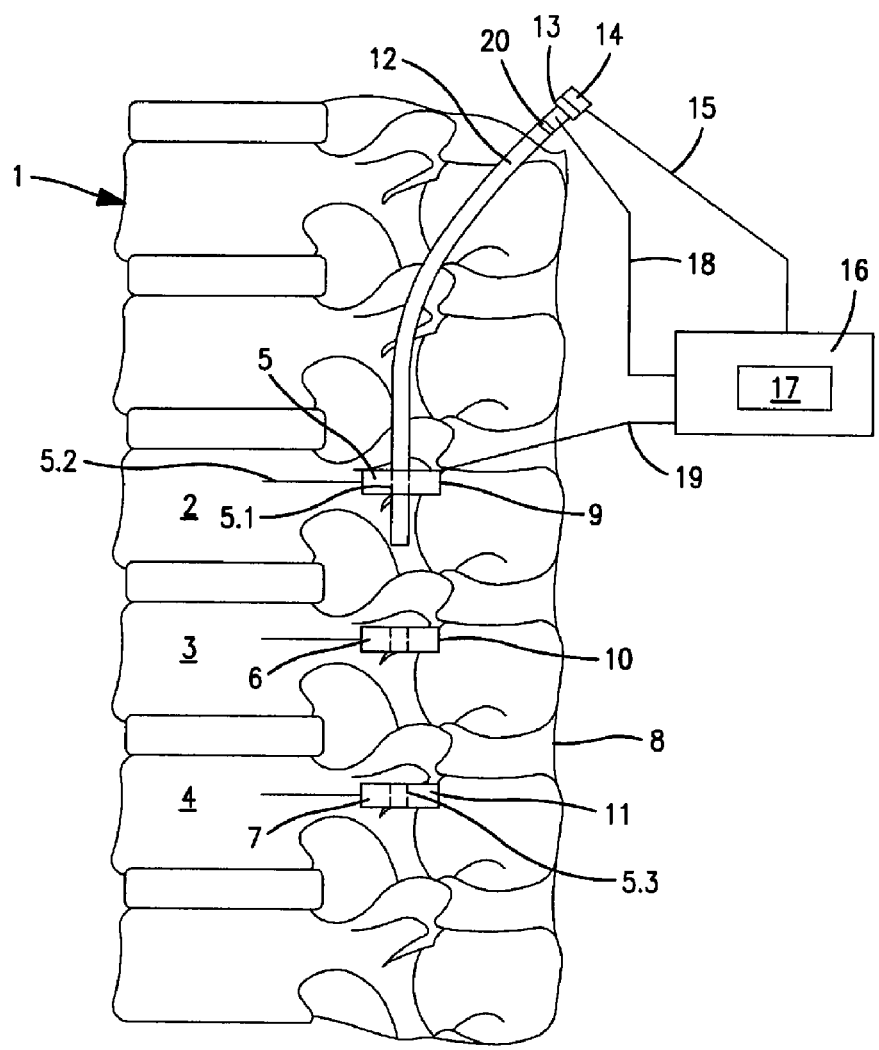
Figure 2:
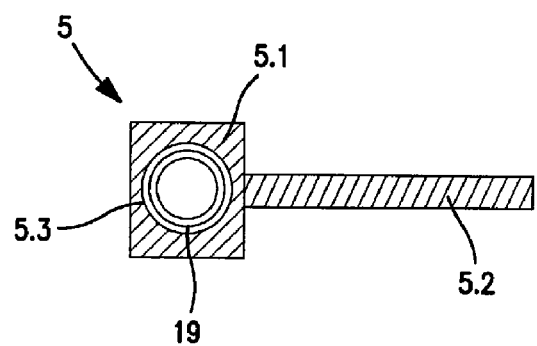
FIG. 2 illustrates the pedicle screws which form the intracorporeal implant used in the method and device of the present invention.

In detail, FIG. 1 shows a lateral portion of a spinal column 1 in three vertebral bodies 2-4 of which so-called pedicle screws 5-7 are screwed, for which purpose the skin designated by 8 has relatively small incisions, indicated by 9-11. The individual pedicle screws 5-7 are composed mainly of, taking the example of the first screw 5, an eyelet 5.1 and a threaded shaft 5.2 and are made of titanium, it also being possible to use chromium/cobalt/nickel alloys.

The three vertebral bodies 2-4 are intended to be connected to one another, i.e. stabilized, for which purpose, according to the minimally invasive method, a fixation rod 12 is used which at its head end has an ultrasound head 13 and a measurement transducer 14, which is connected via an electrical lead 15 to an impedance-measuring device 16 with an optical and/or acoustic display 17. At the same time, the impedance-measuring device 16 is connected via the lead 18 to the fixation rod 12 and via a connector 19 to the eyelet 5.1 of the pedicle screw 5.

The minimally invasive placement of the pedicle screws 5-7 and of the fixation rod 12 takes place as follows. In FIG. 1 only a half of the screw arrangement is shown, since in practice a screw is applied on both sides of the vertebral canal of the vertebral bodies 2-4 concerned, with the result that two rows of screws are present, each with a fixation rod 12, of which, however, only one row can be seen in FIG. 1.

To insert the pedicle screws 5-7, suitably short incisions 9-11 are made in the skin 8, and the pedicle screws 5-7 are screwed, after preliminary drilling, with their respective threaded shaft (example: 5-5.2) into the vertebral bodies 2-4 (example: 2) in such a way that their eyelets (example: 5.1) are horizontal. It should be noted here that the screws 5-7 are placed through the respective muscle, i.e. for this purpose the muscle should if possible be divided longitudinally or pushed aside.

For minimally invasive introduction of the fixation rod 12 through the eyelets of the pedicle screws 5-7, the rod should also if possible be pushed through the muscle. At the start, the skin 8 must be penetrated by an incision (not shown).

To start with, a targeting aid for the fixation rod 12 lies in the impedance measurement in which the measurement parameter used is the phase displacement between current and voltage that can be read off via a display 17, in particular of an optical and/or acoustic nature, i.e. the smaller this phase displacement, the closer the tip of the fixation rod 12 is to the eyelet 5.1. When this "Δ small" has reached a defined near area, the ultrasound head 13 is switched to, since with the latter the fixation rod 12 can be guided with greater precision and thus more easily through the eyelet 5.1.

The continued guiding of the fixation rod 12 through the eyelets of the two further pedicle screws 6 and 7 takes place analogously, and the lead 19 then has to be connected to the eyelet of each of these screws. Two possibilities can be selected here, specifically, in the first case, the impedance method as rough orientation and then, for more precise approach and guiding through the eyelet, ultrasound or both.

The ultrasound head 13 is secured to the measurement transducer 14 on the fixation rod 12 as probe by means of a fine thread, bayonet catch or the like, specifically such that this unit can be removed again at the end of the intervention.

Moreover, the remaining portion of the fixation rod 12 in the spinal column 1 has a notch 20 on its circumference, such that this portion can be removed again in due course with the aid of a suitable extraction instrument.

Overall, therefore, the present invention represents a further milestone in minimally invasive surgery to the benefit of patients.

The invention claimed is:

1. A medical device for determining the position of an intracorporeal implant comprising:
   at least one intracorporeal probe having a hand end and a threaded portion configured to connect to said intracorporeal implant;
   an impedance-measuring device having at least one connector connected to the hand end of the at least one intracorporeal probe and at least one connector configured to connect to said intracorporeal implant, wherein the impedance-measuring device is configured to determine a first position of the intracorporeal implant from the probe by measuring the phase displacement between current and voltage which occurs as a function of distance between the intracorporeal probe and the intracorporeal implant;
   an ultrasound device also connected to the hand end of the at least one intracorporeal probe and configured to determine a second position of the intracorporeal implant from the intracorporeal probe, wherein the second position is closer to the intracorporeal probe than the first position; and
   a switch configured to activate first the impedance-measuring device and thereafter the ultrasound device.

2. The medical device according to claim 1, wherein the switch is further configured to simultaneously activate the impedance-measuring device and the ultrasound device.

3. The medical device according to claim 1, wherein the at least one intracorporeal probe has a rod-shaped design and comprises an ultrasound head and a measurement transducer at the free hand end, wherein the free hand end is not intracorporeal.

4. The medical device according to claim 3, wherein the ultrasound head and the measurement transducer are secured to the at least one intracorporeal probe by the at least one connector connected to the hand end of the at least one intracorporeal probe.

5. The medical device according to claim 3, wherein a portion of the at least one intracorporeal probe has, at least at one end, a notch configured to attach to an extraction instrument.

* * * * *